United States Patent [19]
Takahashi et al.

[11] Patent Number: 5,955,628
[45] Date of Patent: Sep. 21, 1999

[54] TRIMETHYLCATECHOL DIESTER AND A METHOD FOR PRODUCING THE SAME

[75] Inventors: Ikuo Takahashi, Kobe; Masaaki Ito, Himeji, both of Japan

[73] Assignee: Daicel Chemical Industries, Ltd., Osaka, Japan

[21] Appl. No.: 08/991,901

[22] Filed: Dec. 17, 1997

[30] Foreign Application Priority Data

Dec. 27, 1996 [JP] Japan ................................. 8-350457

[51] Int. Cl.$^6$ .................................................. C07C 69/34
[52] U.S. Cl. .............................................. 560/146; 560/86
[58] Field of Search ................................. 560/76, 146, 86

[56] References Cited

U.S. PATENT DOCUMENTS 3,624,134  11/1971  Kablaoui .

FOREIGN PATENT DOCUMENTS 2149159  4/1972  Germany .
477632   4/1972  Japan .
1316739  5/1973  United Kingdom .

OTHER PUBLICATIONS

Frimer et al., J. Org. Chem., 59, 1831–1834 (1994).
Derwent online printout, AN–72–24515, Abstract of DE 2149159, 1972.

*Primary Examiner*—Samuel Barts
*Attorney, Agent, or Firm*—Birch, Stewart, Kolasch & Birch, LLP

[57] ABSTRACT

This method provides a novel trimethylcatechol diester, i.e. 3,4,5-trimethylcatechol diester, at a high yield by reacting 2,6,6-trimethylcyclohexe-2-en-1,4-dione with an acylating agent in the presence of an acid catalyst. The acylating agent includes a $C_{2-4}$ carboxylic acid anhydride (e.g. acetic anhydride) and a $C_{2-4}$ carboxylic acid halide (e.g. acetyl chloride). The catalyst includes a protonic acid and a Lewis acid. Use of a polar solvent (e.g. halogenated hydrocarbon), as the reaction catalyst, results in an enhanced efficiency in the production of the object compound.

4 Claims, 4 Drawing Sheets

TRIMETHYLCATECHOL DIESTER AND A METHOD FOR PRODUCING THE SAME

FIELD OF THE INVENTION

The present invention relates to 3,4,5-trimethylcatechol diester, and a method for producing the same by allowing 2,6,6-trimethylcyclohexe-2-en-1,4-dione (ketoisophorone, KIP) with an acylating agent in the presence of an acid catalyst.

BACKGROUND OF THE INVENTION 3,4,5-trimethylcatechol diester, and its hydrolysed product, trimethylcatechol, have been advantageously used as antioxidants or additives for resins, higher fatty acids, higher alcohols and oils; and raw materials for a monomer, perfumes and pharmaceuticals.

U.S. Pat. No. 3,624,134 discloses that the reaction of α-isophorone with an acylating agent, in the presence of an acid catalyst, provides 3,5,6-trimethylcatechol diester at a yield of 20%. However, this process also yields by-products in large amounts, thus providing the object compound in poor yield. Besides, the compound cannot be separated and purified in a simple manner. As to 3,4,5-trimethylcatechol diester, this literature makes no reference.

Japanese Patent Application Laid-open No. 7632/1972 (JP-A-47-7632) teaches a method for producing trimethylhydroquinone diester by reacting 2,6,6-trimethylcyclohexe-2-en-1,4-dione (ketoisophorone, KIP) with an acylating agent in the presence of a protonic acid catalyst or a Lewis acid catalyst. Neither in this literature is disclosed 3,4,5-trimethylcatechol diester.

SUMMARY OF THE INVENTION

It is therefore an object of the present invention to provide a novel trimethylcatechol diester, i.e. 3,4,5-trimethylcatechol diester, and a method for producing the same.

It is another object of the present invention to provide a method for producing 3,4,5-trimethylcatechol diester at a high yield.

The inventors of the present invention have made intensive researches to accomplish these objects. The present invention provides a novel 3,4,5-trimethylcatechol diester shown by the formula (1),

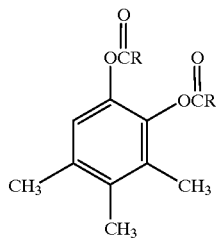

(1)

wherein R represents an alkyl group, a cycloalkyl group, an aryl group or a heterocyclic group. Further, the present invention produces a novel 3,4,5-trimethylcatechol diester shown by the formula (1) by allowing 2,6,6-trimethylcyclohexe-2-en-1,4-dione with an acylating agent in the presence of an acid catalyst.

DETAILED DESCRIPTION OF THE INVENTION

Figure 1:
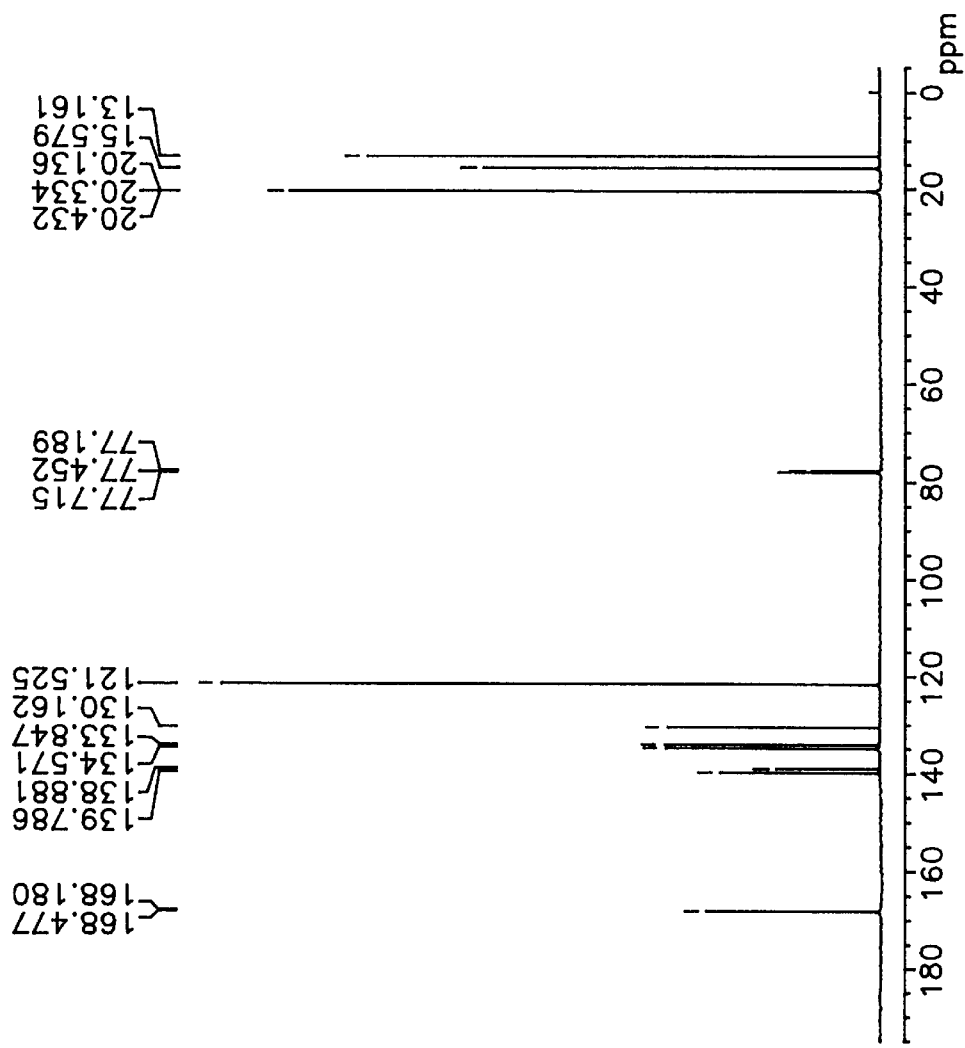
FIG. 1 is a chart showing the $^{13}$C-NMR spectrum of 3,4,5-trimethylcatechol diacetate.

The groups represented by R in the formula (1) are exemplified below. Examples of the alkyl group include a straight (straight-chain) or branched (branched-chain) $C_{1-10}$ alkyl groups (e.g. methyl, ethyl, butyl, isobutyl, tert-butyl, pentyl, hexyl and other $C_{1-8}$ alkyl groups). Examples of the cycloalkyl group include $C_{3-10}$ cycloalkyl groups (e.g. cyclohexyl group). Examples of the aryl group include $C_{6-12}$ aryl groups (e.g. phenyl group, p-methylphenyl group). Examples of the heterocyclic group include aromatic or nonaromatic 5- or 6-membered heterocyclic groups which contain at least one hetero atom selected from a nitrogen, oxygen, or sulfur atom (e.g. furyl group, thienyl group, nicotinyl group, pyridyl group).

Generally, R is a $C_{1-6}$ alkyl group, preferably a $C_{1-4}$ alkyl group, and more preferably a $C_{1-3}$ alkyl group (particularly, a methyl group).

The 3,4,5-trimethylcatechol diester of the formula (1) can be produced in various manners. One of the ideal embodiments is a process which comprises reacting 2,6,6-trimethylcyclohexe-2-en-1,4-dione (ketoisophorone, KIP) with an acylating agent in the presence of an acid catalyst, for the production of 3,4,5-trimethylcatechol diester of the formula (1).

The acid catalyst in this embodiment may be whichever of a protonic acid or a Lewis acid. As the protonic acid, use can be made of organic or inorganic acids (e.g. sulfuric acid, hydrochloric acid, phosphoric acid, fluoroboric acid, hydrogen fluoride or hydrofluoric acid, p-toluenesulfonic acid, benzenesulfonic acid, methanesulfonic acid, chloroacetic acid, picric acid), and super-strong acids which have a Hammett's acidity function $H_0$ of less than −11.93 (e.g. $H_2SO_4$—$SO_3$,HF—$NbF_5$, HF—$TaF_5$, $SbF_5$, HF—$SbF_5$, $SbF_5$—$FSO_3H$, $FSO_3H$—$TaF_5$, $SbF_5$—$CF_3SO_3H$). As the Lewis acid, use can be made of $BF_3$, $BF_3OEt_2$, $AlCl_3$, $FeCl_3$, $ZnCl_2$, $TiCl_4$, $SnCl_2$, etc.

The amount of the catalyst only needs to be in the range of effective amounts, depending on the reaction conditions. For example, the amount of the catalyst is 0.001 to 100 parts by weight, preferably about 0.01 to 10 parts by weight (e.g. 0.05 to 10 parts by weight), and more preferably about 0.1 to 5 parts by weight, relative to 100 parts by weight of the substrate KIP. Generally, the amount of the catalyst can be selected from the range of about 0.001 to 20 mol %, preferably about 0.01 to 15 mol %, based on the amount of the substrate KIP.

Solid catalysts (particularly, solid acid catalysts) can be used as the catalyst. For example, the solid acid catalysts include strongly acidic ion exchange resins (e.g. porous or nonporous ion exchange resins having a sulfonic acid group), super-strongly acidic ion exchange resins (e.g. porous or nonporous ion exchange resins having a super-strong acid group such as —$CF_2CF_2SO_3H$), sulfates (e.g. $CaSO_4$, $Fe_2(SO_4)_3$, $CuSO_4$, $NiSO_4$, $AlSO_4$, $MnSO_4$, $BaSO_4$, $CoSO_4$, $ZnSO_4$, $(NH_4)_2SO_4$), metal oxides (e.g. $SiO_2$, $Al_2O_3$, $TiO_2$, $Fe_2O_3$, $ZrO_2$, $SnO_2$), compound oxides (e.g. $SiO_2$—$Al_2O_3$, $SiO_2$—$TiO_2$, $TiO_2$—$ZrO_2$, $SiO_2$—$ZrO_2$), zeolites (e.g. Y-, X-, or A-type zeolite having an acidic OH group, ZSM5, moldenite, VPI5, AlPO$_4$-5, AlPO$_4$-11), kaolins, and heteropoly acids (e.g. heteropoly acids having an element such as P, Mo, V, W, and Si).

Among the solid acid catalysts, a specific example of the strongly acidic ion exchange resin is a styrene-divinylbenzenesulfonic acid-series ion exchange resin, "Amberlyst 15" (manufactured by Organo, Ltd.), and specific examples of the superstrongly acidic ion exchange resin include a fluorinated sulfonic acid-series resin, "Nafion NR50" (Aldrich, Inc.), "Nafion H" (Dupont, Inc.), etc.

The solid acid catalyst may be a solid acid catalyst which supports or holds a protonic acid (e.g. the above-mentioned superstrong acids and other protonic acids; strong acids) or a Lewis acid on a support (or a carrier) or a porous support (or carrier). As the acids to be supported (acid catalysts), there may be mentioned SbF$_5$, TaF$_5$, BF$_3$, AlCl$_3$, AlBr$_3$, SbF$_5$—HF, SbF$_5$—FSO$_3$H, SbF$_5$—CF$_3$SO$_3$H, SO$_4^{2-}$, and tungstic acid.

The support may be either porous or non-porous. Examples of the support are metal oxides (e.g. SiO$_2$, Al$_2$O$_3$, TiO$_2$, Fe$_2$O$_3$, ZrO$_2$, SnO2), compound oxides (e.g. SiO$_2$—Al$_2$O$_3$, SiO$_2$—TiO$_2$, TiO$_2$—ZrO$_2$, SiO$_2$—ZrO$_2$), zeolites, graphites, Pt-graphites, ion exchange resins, metal sulfates, metal chlorides, metals (e.g. Pt, Au), alloys (e.g. Pt—Au, Ni—Mo, Al—Mg), polymers, salts (e.g. SbF$_3$, AlF$_3$), bauxites, activated carbons, charcoals and the like. The porous support is not specifically restricted in its surface area (e.g. 10 to 5,000 m$^2$/g), pore volume, and average pore diameter. The amount of the acid catalyst to be supported is, for instance, about 0.1 to 50% by weight, preferably about 1 to 25% by weight.

To be specific, the catalyst to be supported include SbF$_5$/SiO$_2$, SbF$_5$/Al$_2$O$_3$, SbF$_5$/TiO$_2$, SbF$_5$/Fe$_2$O$_3$, SbF$_5$/ZrO$_2$, SbF$_5$/SnO$_2$, SbF$_5$/SiO$_2$—Al$_2$O$_3$, SbF$_5$/SiO$_2$—TiO$_2$, SbF$_5$/TiO$_s$—ZrO$_2$, SbF$_5$/SiO$_2$—ZrO$_2$, AlCl$_3$/CuSO$_4$, SbF$_5$—HF/Al$_2$O$_3$, SbF$_5$—HF/SiO$_2$—Al$_2$O$_3$, SbF$_5$—HF/activated carbon, SbF$_5$—FSO$_3$H/Al$_2$O$_3$, SbF$_5$—FSO$_3$H/SiO$_2$—Al$_2$O$_3$, SbF$_5$FSO$_3$H/activated carbon, SO$_4^{2-}$/ZrO$_2$ (sulfated zirconia), SO$_4^{2-}$/TiO$_2$ (sulfated titania), SO$_4^{2-}$/Fe$_2$O$_3$, SO$_4^{2-}$/TiO$_2$—ZrO$_2$WO$_3$/ZrO$_2$, Pt/SO$_4^{2-}$/ZrO$_2$, and others.

The amount of the solid acid catalyst is determined, in accordance with the reaction conditions, in the range of effective amounts. For example, the amount is about 0.1 to 1,000 parts by weight, preferably about 1 to 100 parts by weight (e.g. 5 to 100 parts by weight), and more preferably about 2 to 50 parts by weight (e.g. 5 to 25 parts by weight), relative to 100 parts by weight of the substrate (e.g. KIP).

The solid catalyst may be used as a slurry in the reaction system, or may be charged in a column in which reactants are able to flow.

As the acylating agent, use may be made of an acylating agent containing an aliphatic hydrocarbon group, an alicyclic hydrocarbon group, an aromatic hydrocarbon group or a heterocyclic group, each of which corresponds to R in the formula (1). Specific examples of the acylating agent include acid anhydrides, acyl halides, enol esters, and the like.

As the acid anhydrides, there may be mentioned carboxylic acid anhydrides including, for instance, straight or branched C$_{1-10}$ alkyl-carboxylic acids (e.g. C$_{1-8}$ alkyl-carboxylic acids such as acetic acid, propionic acid, butyric acid, isobutyric acid, and valeric acid, particularly C$_{1-6}$ alkyl-carboxylic acids), alicyclic carboxylic acids (e.g. C$_{3-10}$ cycloalkyl-carboxylic acids such as cyclohexanecarboxylic acid), aromatic carboxylic acids (e.g. C$_{6-12}$ aryl-carboxylic acids such as benzoic acid and toluic acid), halogen-containing carboxylic acids (e.g. chloroacetic acid, trichloroacetic acid, trifluoroacetic acid), heterocyclic carboxylic acids (e.g. furancarboxylic acid, thiophenecarboxylic acid, nicotinic acid, pyridinecarboxylic acid), and other anhydrides. In particular, C$_{1-4}$ alkyl-carboxylic acid anhydrides (e.g. C$_{2-4}$ carboxylic acid anhydrides such as acetic anhydride and propionic anhydride) are preferred among these.

As the acyl halides, there may be exemplified acyl halides which correspond to the above-mentioned acid anhydrides, including C$_{1-10}$ alkyl-carboxylic acid halides (e.g. C$_{1-8}$ alkyl-carboxylic acid halide such as acetyl chloride, propionyl chloride, and butyryl chloride), alicyclic carboxylic acid halides (e.g. cyclohexanecarboxylic acid halide), aromatic carboxylic acid halides (e.g. benzoic acid halide), heterocyclic carboxylic acid halides (e.g. furancarboxylic acid halide), and the like. Among them, C$_{1-4}$ alkyl-carboxylic acid halides (e.g. C$_{2-4}$ carboxylic acid halides such as acetyl chloride and propionyl chloride) are desirable. As the enol esters, there may be mentioned isopropenyl acetate, isopropenyl propionate, isopropenyl isobutyrate, isopropenyl butyrate, cyclohexenyl benzoate, and so on.

These acylating agents can be used in a molar quantity of at least about twice (e.g. 2 to 10 times), preferably about 3 to 10 times, relative to the substrate KIP. An excess amount of the acylating agent may be used as the solvent.

The reaction of the present invention may be conducted in the presence of or the absence of a solvent. Inert solvents include straight or branched, saturated or unsaturated hydrocarbons (e.g. aliphatic hydrocarbons including hexane, heptane, and octane; alicyclic hydrocarbons including cyclohexane; unsaturated aliphatic or alicyclic hydrocarbons including octene and cyclohexene; aromatic hydrocarbons including benzene, toluene, and xylene), organic acids (e.g. acetic acid, propionic acid, butyric acid, lactic acid, trichloroacetic acid, trifluoroacetic acid), esters (e.g. methyl acetate, ethyl acetate, butyl acetate), halogen-containing solvents (e.g. methylene chloride, chloroform, carbon tetrachloride, 1,2-dichloroethane, chlorobenzene, dichlorobenzene), ethers (e.g. diethyl ether, diisopropyl ether, dibutyl ether, tetrahydrofuran, dioxane, ethylene glycol dimethyl ether, diethylene glycol dimethyl ether), ketones (e.g. acetone, methyl ethyl ketone, methyl isobutyl ketone, diisobutyl ketone, cyclohexanone), nonprotonic polar solvents (e.g. amides including dimethylformamide and dimethylacetoamide; amines including N-methylpyrrolidone; sulfoxides including dimethylsulfoxide; nitrites including acetonitrile and benzonitrile; nitroes including nitromethane, nitroethane, and nitrobenzene), etc. These solvents can be used alone or as a mixture of two or more species.

In order to provide the compound of the formula (1) at a high conversion and selectivity, it is advisable to carry out the reaction in the presence of an inert polar solvent. The dipole moment (Debye=3.3356×10$^{-30}$ Cm) of the polar solvent is about 1.0 or higher (e.g. 1 to 5), preferably about 1.2 to 4 (e.g. 1.3 to 3.5).

Such polar solvents include the halogenated hydrocarbons, organic acids, esters, ethers, ketones, amides or amines, sulfoxides, nitrites, and nitro compounds, which have been mentioned above.

These polar solvents can be used alone or in combination. They may also be used together with a non-polar solvent.

In the reaction system of the present invention, the concentration of the substrate, 2,6,6-trimethylcyclohexe-2-en-1,4-dione, is not strictly limited. For instance, the concentration may be about 5 to 50% by weight (e.g. 5 to 40% by weight), preferably about 10 to 45% by weight (e.g. 10 to 35% by weight).

The reaction temperature can be selected from the range of about 0 to 150° C., preferably about 10 to 120° C. (e.g. 10 to 100° C.). Practically, the reaction temperature is about 50 to 110° C. If the reaction temperature is too high, the object compound may be coloured and be produced only in a lower yield. On the other hand, if the temperature is too low, the reaction may proceed at an extremely slow rate.

After the reaction has completed, the reaction mixture is separated and purified by a conventional process (e.g. filtration, concentration, distillation, crystallisation, extraction, or a combination of these processes) to give 3,4,5-trimethylcatechol diester.

It is also possible to obtain 3,4,5-trimethylcatechol by allowing a reaction mixture containing trimethylcatechol diester to undergo a hydrolysis step.

Thus, the present invention provides a novel 3,4,5-trimethylcatechol diester, which can be produced at a high yield by way of an esterification reaction of 2,6,6-trimethycyclohexa-2-en-1,4-dione.

The following examples are intended to illustrate the present invention in more detail but should by no means limit the scope of the invention.

EXAMPLES

Example 1

Charged into a three-neck flask (capacity: 300 ml) were 10 g of a strongly acidic ion exchange resin "Amberlyst 15" (manufactured by Organo, Ltd.) as the catalyst, 30 g (0.197 mole) of ketoisophorone, 46.4 g (0.591 mole) of acetyl chloride, and 160 ml of 1,2-dichloroethane. The mixture was allowed to react for six hours at 85° C. After the completion of the reaction, a gas chromatographic analysis showed that the ketoisophorone, the raw material, was completely consumed (conversion: 100%), and that 3,4,5-trimethylcatechol diacetate was produced at a yield of 65%. The catalyst was separated from the reaction mixture by filtration, and then the filtrate was concentrated. Using a mixed solvent of ethyl acetate and hexane (ethyl acetate/hexane=1/4 (by volume)), the concentrated filtrate was crystallized to give white needle crystals of 3,4,5-trimethylcatechol diacetate at a yield of 36%, whose melting point was between 119 and 120° C.

The structure of the thus obtained compound was analyzed by $^{13}$C-NMR (CDCl$_3$), the infrared absorption spectrum (IR spectrum), and the mass spectrometric analysis. The apparatus employed were "JNM-A 500 NMR measuring apparatus" (manufactured by JEOL) for the NMR, "FT IR-8100M measuring apparatus" (manufactured by Shimadzu Corporation) for the IR spectrum, and "HP 5989B measuring apparatus" (manufactured by Hurlett-Packard) as the mass spectrometer were employed.

The results of the $^{13}$C-NMR measurement were as follows:

Signal derived from an aromatic carbon bonded with an acetoxy group at the 1-position: 139.7 ppm;
Signal derived from a carbon bonded with an acetoxy group at the 2-position: 138.9 ppm;
Signals derived from carbons bonded with methyl groups at the 3-, 4-, and 5-positions each:
130.1 ppm, 133.8 ppm, 134.6 ppm;
Signal derived from a carbon bonded with hydrogen at the 6-position: 121.5 ppm;
Signals derived from a carbon of the carbonyl in the acetyl group: 168.2 ppm, 168.5 ppm.

Figure 2:
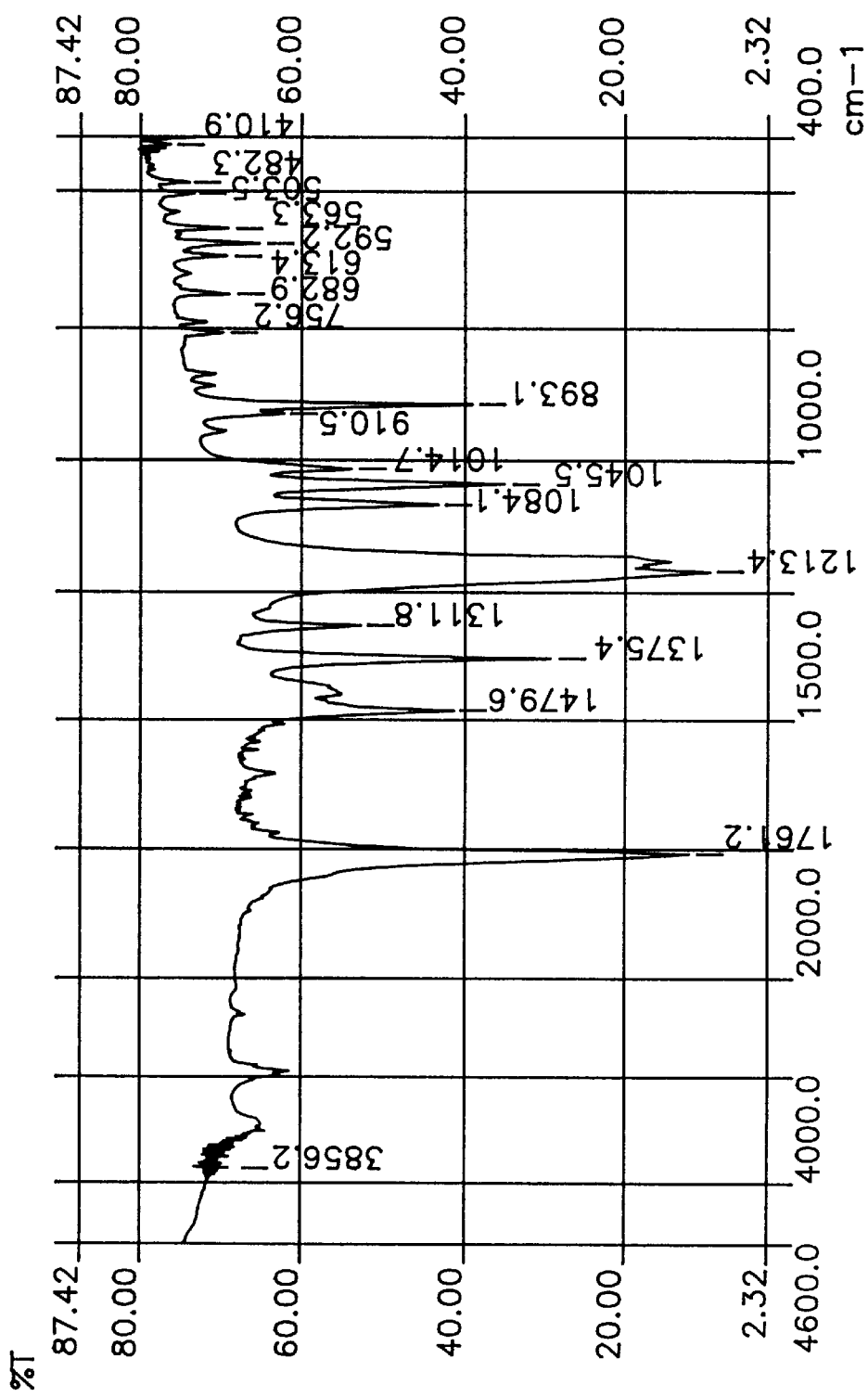
FIG. 2 is a chart showing the infrared absorption spectrum of 3,4,5-trimethylcatechol diacetate.
Figure 3:
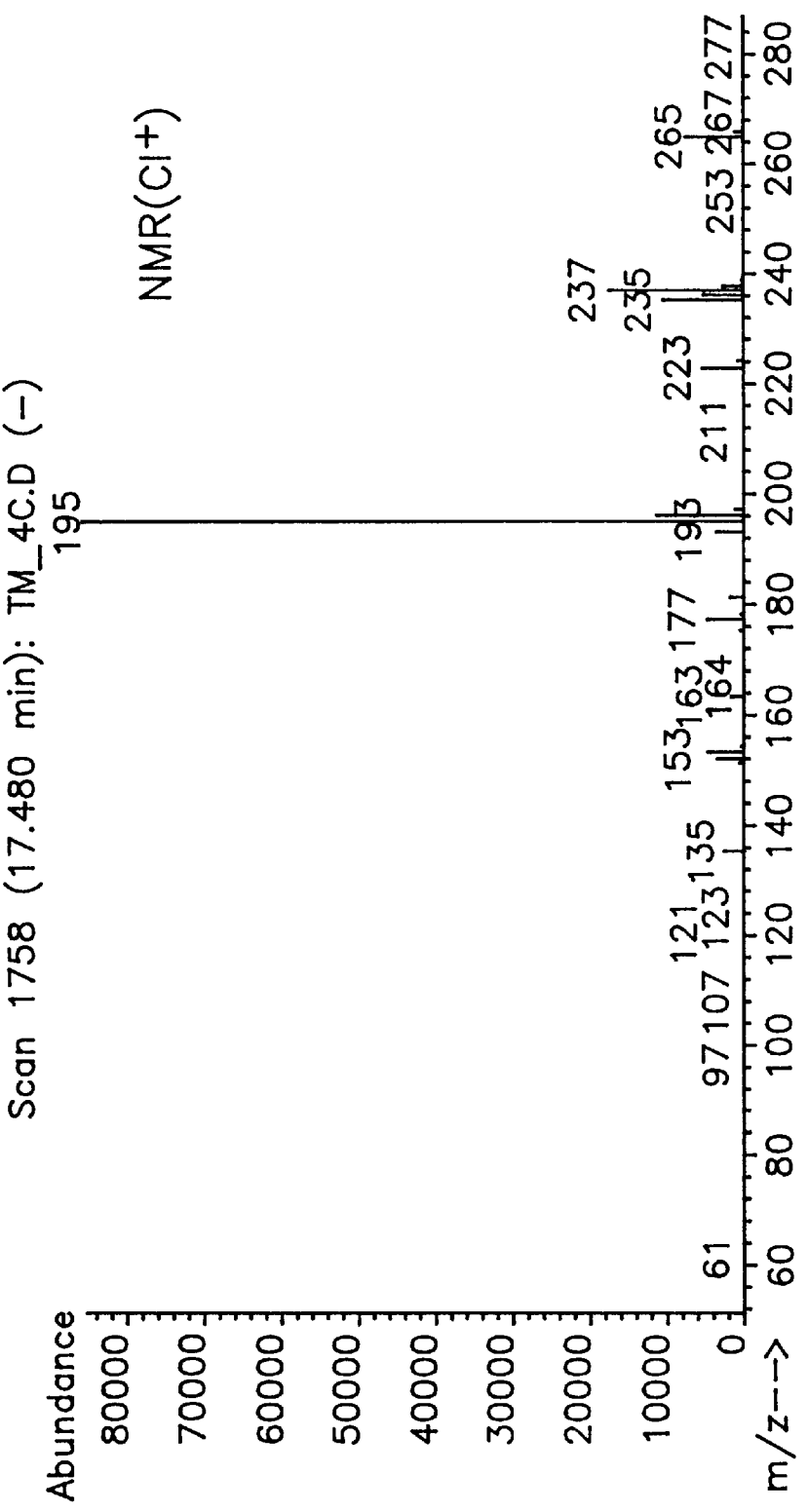
FIG. 3 is a chart showing the mass spectrum ($CI^+$) of 3,4,5-trimethylcatechol diacetate.
Figure 4:
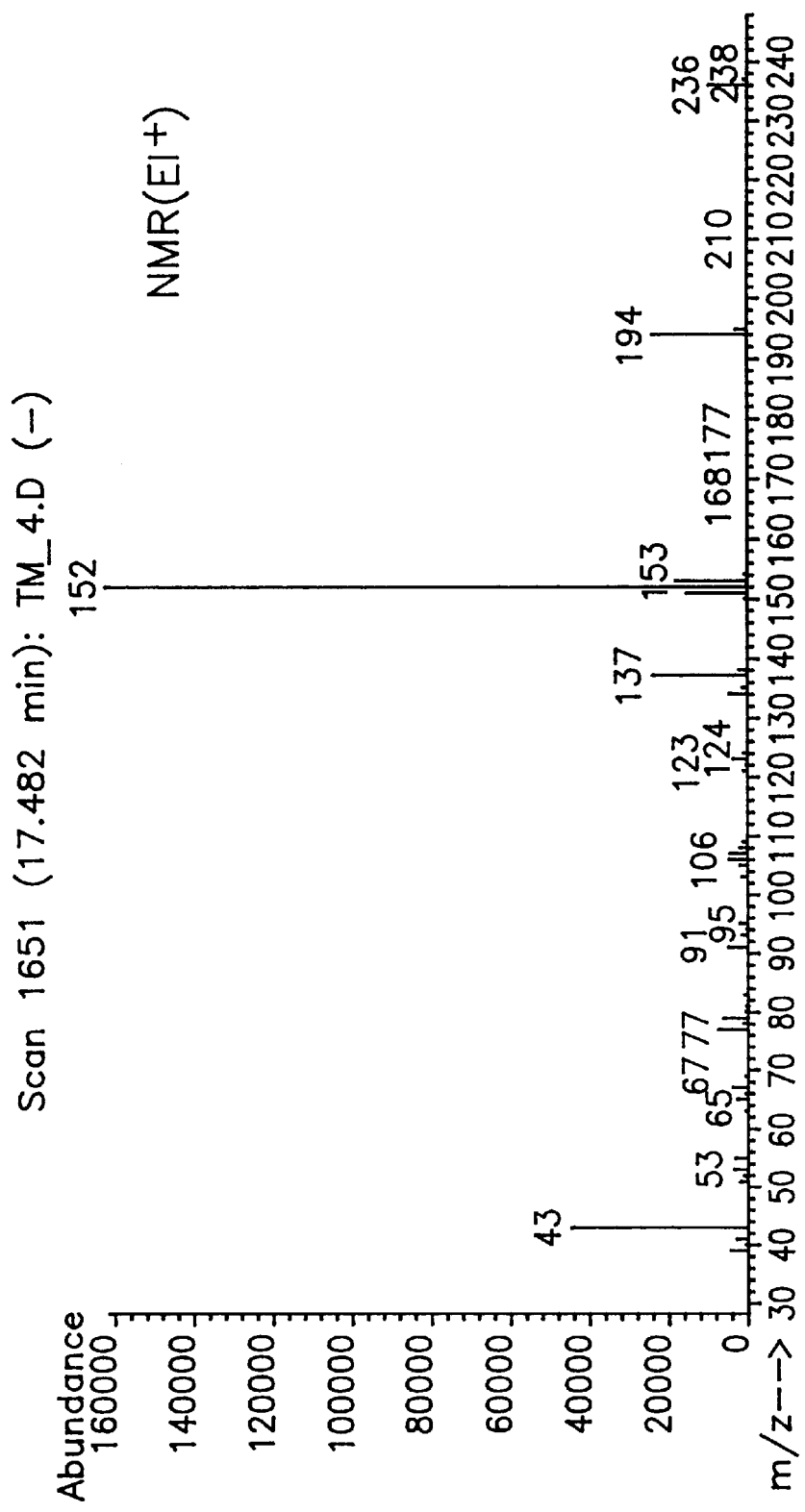
FIG. 4 is a chart showing the mass spectrum ($EI^+$) of 3,4,5-trimethylcatechol diacetate.

The results of the analyses of the 3,4,5-trimethylcatechol diacetate were compiled in the charts: the $^{13}$C-NMR analysis in FIG. 1, the IR spectrum analysis in FIG. 2, and the mass spectrum by the mass spectrometric analysis in FIGS. 3 (CI$^+$) and 4 (EI$^+$).

Example 2

The reaction process of Example 1 was followed, except for using 80.4 g (0.788 mole) of acetic anhydride instead of acetyl chloride and performing the reaction for eight hours at 85° C. Gas chromatography after the reaction proved complete consumption of the raw-material ketoisophorone and production of 3,4,5-trimethylcatechol diacetate at a yield of 32%. After being separated from the catalyst by filtration, the filtrate was concentrated, and thereafter crystallized with the use of an ethyl acetate/hexane solvent (1/4 by volume). Thus obtained were white needle crystals of 3,4,5-trimethylcatechol diacetate at a yield of 17% (melting point: 119 to 120° C.). The structure of the crystals was analyzed by $^{13}$C-NMR (CDCl$_3$), the infrared absorption spectrum (IR spectrum), and the mass spectrometric analysis, which presented similar results to those in Example 1.

Example 3

The process of Example 1 was repeated except for employing 5.0 g (9.2 mole) of sulfuric acid instead of the strongly acidic ion exchange resin "Amberlyst 15" and allowing the reaction for eight hours at 80° C. A gas chromatographic analysis after the completion of the reaction proved complete consumption of the material ketoisophorone, and production of 3,4,5-trimethylcatechol diacetate at 28% yield. The reaction mixture was neutralized with the use of a 1N—NaOH aqueous solution, and separated by extraction. After being concentrated, the concentrate was crystallized by means of an ethyl acetate/hexane solvent (1/3 by volume) to give white needle crystals of 3,4,5-trimethylcatechol diacetate (melting point: 119 to 120° C.) at a yield of 15%. The structure of the crystals was analysed by $^{13}$C-NMR (CDCl$_3$), the infrared absorption spectrum (IR spectrum), and the mass spectrometric analysis, which presented similar results to those in Example 1.

Example 4

The catalyst used in Example 1, which was filtered out of the reaction mixture, washed with methanol, and dried, was reutilized. After the completion of a reaction conducted in the same manner as in Example 1, gas chromatography of the reaction mixture showed complete consumption of the material ketoisophorone, and production of 3,4,5-trimethylcatechol diacetate at a yield of 61%.

Example 5

Charged into a 100-ml three-neck flask were 5 g of a super-strongly acidic ion exchange resin "Nafion NR50" (manufactured by Aldrich, Inc.) as the catalyst, 10 g (0.066 mole) of ketoisophorone, 19.6 g (0.25 mole) of acetyl chloride, and 40 ml of 1,2-dichloroethane. The mixture was allowed to react for 10 hours at 85° C. After the completion of the reaction, a gas chromatographic analysis showed that the ketoisophorone, the raw material, was completely consumed, and that 3,4,5-trimethylcatechol diacetate was produced at a yield of 51%. The catalyst was separated from the reaction mixture by filtration. The filtrate was concentrated and then crystallized using a mixed solvent of ethyl acetate and hexane (ethyl acetate/hexane=1/4 (by volume)). This process provided white needle crystals of 3,4,5-trimethylcatechol diacetate at a yield of 31%, whose melting point was between 119 and 120° C.

Example 6

Charged into into a 100-ml three-neck flask were 1 g of a protonic Y-type zeolite (Si/Al=5) as the catalyst, 10 g (0.066 mole) of ketoisophorone, 19.6 g (0.25 mole) of acetyl chloride, and 40 ml of dichlorobenzene. The mixture was allowed to react for 16 hours at 100° C. After the reaction, the reaction mixture was treated in the same manner as in Example 1, and there-after crystallized to give 3,4,5-trimethylcatechol diacetate at a yield of 9%.

Example 7

Charged into a 100-ml three-neck flask were 1 g of sulfuric acid/zirconia as the catalyst, 5 g (0.033 mole) of ketoisophorone, 30 g (0.293 mole) of acetic anhydride, and 30 ml of chlorobenzene. The mixture was allowed to react for 10 hours at 90° C. A gas chromatographic analysis after the reaction showed 48% consumption of the ketoisophorone, the raw material, and 27% yield of 3,4,5-trimethylcatechol diacetate.

Example 8

After repeating the reaction of Example 1 and observing complete consumption of the material ketoisophorone, water (50 g) was added to the reaction mixture, which was allowed to undergo a hydrolysis reaction at 90° C. for 12 hours. After the completion of the reaction, gas chromatography found no 3,4,5-trimethylcatechol diacetate, but provided 3,4,5-trimethylcatechol at a yield of 60%. The reaction mixture was filtered to remove the catalyst. The filtrate was concentrated and then crystallized using ethanol and water, which gave 3,4,5-trimethylcatechol at a yield of 33%.

What is claimed is:

1. A method for producing 3,4,5-trimethylcatechol diester shown by the formula (1),

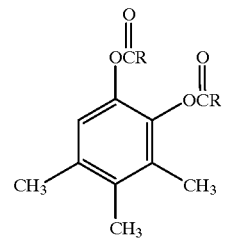

(1)

wherein R represents an alkyl group, a cycloalkyl group, an aryl group or a heterocyclic group, by allowing 2,6,6-trimethylcyclohex-2-en-1,4-dione to react with an acylating agent in the presence of a solid acid catalyst and an inert polar solvent having a dipole moment (Debye) of 1.0 or higher, wherein said inert polar solvent is at least one solvent selected from the group consisting of halogenated hydrocarbons, organic acids, esters, ethers, ketones, amides, amines, sulfoxides and nitrites.

2. A method as claimed in claim 1, wherein said acylating agent is a $C_{2-4}$ carboxylic acid anhydride or a $C_{2-4}$ carboxylic acid halide.

3. A method as claimed in claim 1, wherein said acylating agent is acetic anhydride or acetyl chloride.

4. A method as claimed in claim 1, wherein said inert polar solvent is a halogenated hydrocarbon.

* * * * *